United States Patent
Gaines et al.

(10) Patent No.: US 9,320,361 B2
(45) Date of Patent: Apr. 26, 2016

(54) APPARATUS AND METHOD FOR TESTING A CLIMATE CONTROLLED VEHICLE SEAT

(71) Applicant: Ford Global Technologies, LLC, Dearborn, MI (US)

(72) Inventors: David William Gaines, Farmington, MI (US); Anton Crainic, Canton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 296 days.

(21) Appl. No.: 13/961,153

(22) Filed: Aug. 7, 2013

(65) Prior Publication Data
US 2015/0040643 A1    Feb. 12, 2015

(51) Int. Cl.
*G01N 3/12* (2006.01)
*A47C 7/74* (2006.01)
*G01M 99/00* (2011.01)
*G01R 19/00* (2006.01)
*B60N 2/56* (2006.01)

(52) U.S. Cl.
CPC .............. *A47C 7/744* (2013.01); *B60N 2/565* (2013.01); *B60N 2/5657* (2013.01); *G01M 99/001* (2013.01); *G01M 99/002* (2013.01); *G01M 99/008* (2013.01); *G01N 3/12* (2013.01); *G01R 19/0092* (2013.01)

(58) Field of Classification Search
CPC ....... A47C 7/744; B60N 2/00; G01M 99/001; G01M 99/002; G01M 99/008; G01R 19/0092; G01N 3/12
See application file for complete search history.

(56) References Cited

U.S. PATENT DOCUMENTS

| | | | | |
|---|---|---|---|---|
| 4,676,091 A | * | 6/1987 | Schuster | G01N 15/0826 73/37.7 |
| 4,756,183 A | * | 7/1988 | Rajala | G01N 15/082 73/37.7 |
| 2013/0137354 A1 | * | 5/2013 | Tsuzaki | B60H 1/00457 454/75 |

FOREIGN PATENT DOCUMENTS

| | | |
|---|---|---|
| DE | 10210149 A1 | 9/2003 |
| DE | 10332504 B4 | 4/2006 |
| KR | 1020060001080 A | 1/2006 |

OTHER PUBLICATIONS

Machine translation of KR1020040050102 downloaded Sep. 8, 2015.*

* cited by examiner

*Primary Examiner* — Peter Macchiarolo
*Assistant Examiner* — Natalie Huls
(74) *Attorney, Agent, or Firm* — Vichit Chea; Brooks Kushman P.C.

(57) ABSTRACT

A climate controlled seat test apparatus is provided. The test apparatus may have a pump arrangement configured to alter a pressure within a vicinity of a climate controlled portion of a vehicle seat. A controller may be programmed to detect airflow obstructions or losses within the climate controlled portion of the seat. The climate controlled portion may include a blower motor. The controller may detect airflow obstructions and/or losses based on a change in current consumed by the blower motor caused by the pump arrangement altering the pressure within the vicinity of the climate controlled portion.

12 Claims, 3 Drawing Sheets

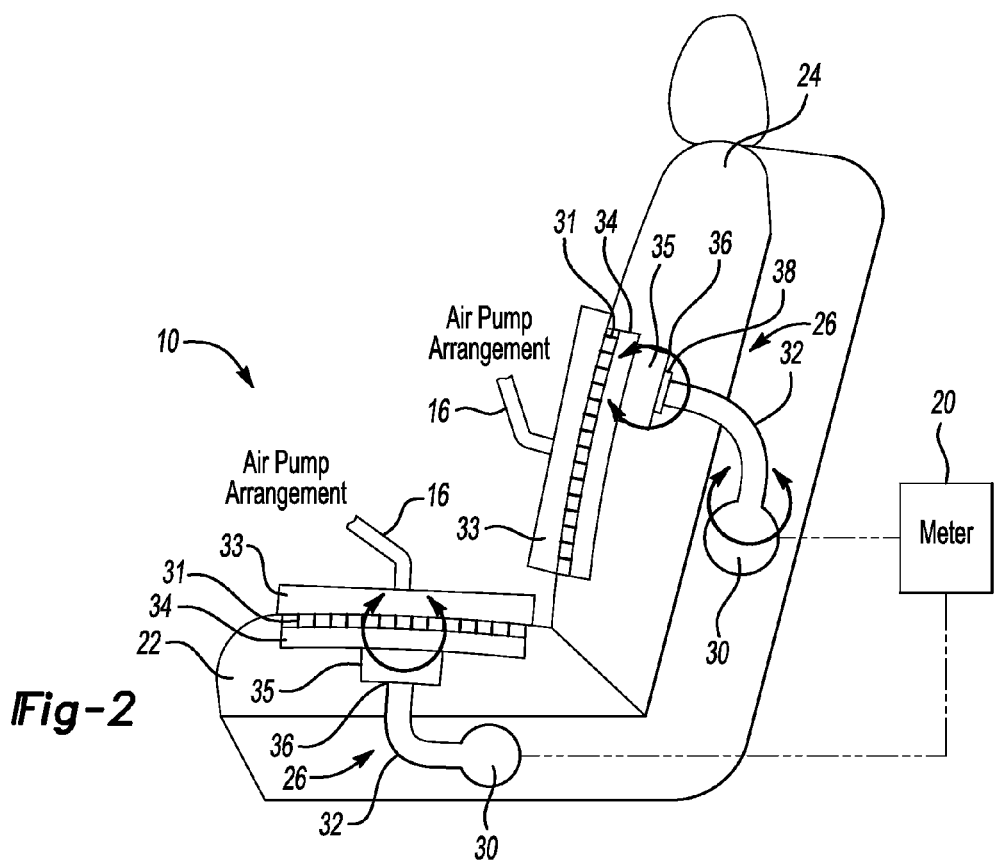
Fig-2
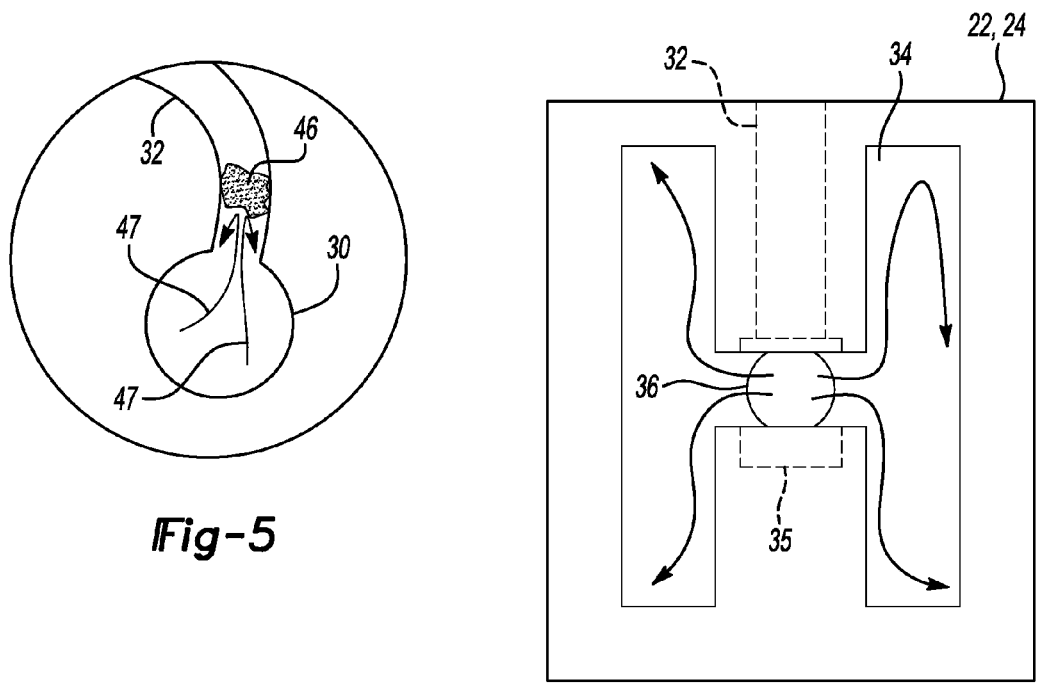
Fig-5
Fig-6

APPARATUS AND METHOD FOR TESTING A CLIMATE CONTROLLED VEHICLE SEAT

TECHNICAL FIELD

The disclosure relates to testing airflow within climate control systems for vehicle seats.

BACKGROUND

Automotive vehicles include capabilities to heat and cool vehicle occupants, such as climate controlled vehicle seats. Occupant controls and/or a controller may direct operation of these climate control systems to heat and/or cool occupants. The climate control systems may use modules to heat/cool airflow and blowers to direct the airflow to the occupant when operating properly.

SUMMARY

A climate controlled seat test apparatus includes a plenum adapted to be placed against an A-surface trim cover of a climate controlled portion of a vehicle seat. A chamber is formed between the plenum and A-surface trim cover. An air pump arrangement is configured to alter a pressure within the chamber. The climate controlled portion of the vehicle seat includes a blower motor. A controller is programmed to detect obstructions to or losses of airflow between the A-surface trim cover and the blower motor based on a change in current consumed by the blower motor caused by a change in pressure within the chamber.

A method for testing a climate controlled seat includes positioning a plenum against a climate controlled portion of a seat to form a chamber between the plenum and the climate controlled portion. The climate controlled portion includes a blower motor. The method also includes capturing a first current reading of the blower motor while the blower motor is on and a pressure within the chamber is at a first pressure level. The method further includes capturing a second current reading of the blower motor while the blower motor is on and a pressure within the chamber is at a second pressure level. In response to an absolute current draw difference between the first and second current readings being less than a threshold value, outputting a signal indicating that the climate controlled portion has an airflow fault condition.

A vehicle seat test apparatus includes a pump arrangement configured to alter a pressure within a vicinity of a climate controlled portion of a seat. The seat test apparatus also includes at least one controller programmed to detect airflow obstructions or losses within the climate controlled portion. The climate controlled portion includes a blower motor. The seat test apparatus detects airflow obstructions or losses based on a change in current consumed by the blower motor caused by the pump arrangement altering the pressure within the vicinity of the climate controlled portion.

BRIEF DESCRIPTION OF THE DRAWINGS

FIG. 2 is a side view, in cross-section, of a test apparatus and climate control system of a vehicle seat.

FIG. 5 is a side view, in cross-section, of an airflow fault condition in which debris is obstructing a channel within a climate control system of a vehicle seat.

FIG. 6 is a plan view, in cross-section, of an airflow channel within a climate control system of a vehicle seat.

DETAILED DESCRIPTION

Figure 1:
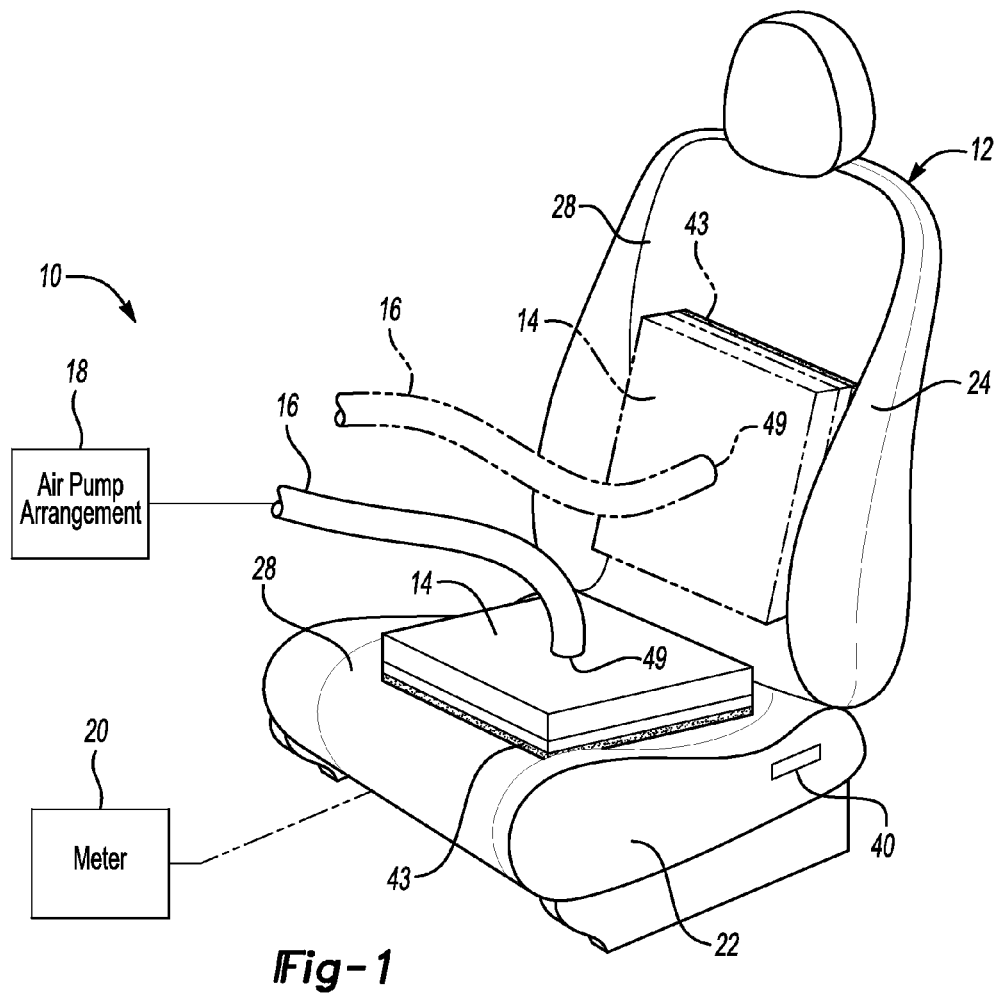
FIG. 1 is a perspective view of a test apparatus for a climate controlled vehicle seat.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Automotive vehicle seats have features including climate control systems positioned within the cushion and seatback of a seat. These climate control systems may include heating, cooling and/or heating/cooling capabilities. A heat panel is one example of a device used by climate control systems to warm a seat occupant and is typically positioned below the surface or trim of the cushion and/or seatback. More recently, climate control systems use airflow to provide both heating and cooling capabilities. One climate control system example includes a thermal electric device module ("TED") to heat/cool air and a blower or fan to direct air through the TED and climate control system to reach the seat occupant. A controller may facilitate operation of the TED and blower, including control of air temperature and airflow. The controller may be in communication with one or more occupant controls and/or the controller may operate according to preprogrammed instructions. When the climate control system is operating properly, the occupant may select a desired temperature to initiate a corresponding output from the TED and blower to warm or cool the occupant when sitting on the seat. However, errors in assembling components of the climate control system may cause improper operation and/or may prevent operation altogether.

Airflow fault conditions, for example, may disrupt operation and airflow. One cause for these airflow fault conditions may include improper assembly of the climate control system components. The improper assembly may result in airflow blockage and/or airflow leakage within the climate control system. It may be difficult and/or time consuming to evaluate airflow within the climate control system once the seat is assembled and/or is installed onto a vehicle.

Assembly of the climate control system and seat may occur in multiple steps prior to installing the seat onto a vehicle at a vehicle assembly plant. The assembly of the seat itself may take place at a separate facility, such as a just in time facility ("JIT facility"), and prior to delivery to the vehicle assembly plant. While the vehicle assembly plant may test and/or evaluate operation of the climate control system on the assembly line, once the seat is installed onto the vehicle it may be difficult and/or time consuming to correct any airflow fault conditions that may be identified, such as obstructed airflow or leakage. The fault conditions may require tasks such as seat teardown and/or seat removal from the vehicle along with disconnection of any related wiring to the controller or occupant controls. Climate variables may further impair the accuracy of testing the climate control systems within seats. Two climate variable examples include a high temperature and high humidity of the vehicle assembly plant.

Operating test and repair stations on the assembly line increases costs for the vehicle assembly plant. To evaluate airflow, climate control system test methods may require operator time associated with setup, evaluation and repair. For example, one portion of a TED test setup may require between three and five minutes for the TED to reach a desired test temperature. Once the TED reaches the desired temperature, evaluation and related repair time may further increase operator time spent and costs. It may be desirable to provide a test apparatus and/or algorithm to assist in identifying airflow fault conditions within climate control systems of vehicle seats.

FIGS. 1 through 6 show an illustrative test apparatus 10 for an automotive vehicle seat 12 having a climate control system. The test apparatus 10 may include a plenum 14, a delivery tube 16, an air pump arrangement 18 and a current meter 20. Examples of the air pump arrangement 18 may include devices with capabilities to alter and/or influence pressure levels within a fluid system such as vacuums and/or air pumps. As such, the air pump arrangement 18 may have one way airflow delivery and/or two way airflow delivery. The seat 12 may include a cushion 22, a seatback 24, and one or more climate control systems 26. The cushion 22 and seatback 24 both include an A-surface trim cover 28. The climate control system 26 may include trim holes 29 of the trim cover 28 and a seat support portion 31 with one or more support portion holes 27. The support portion 31 may be positioned against and/or adjacent to the trim cover 28. When positioned against the trim cover 28, the plenum 14 and trim cover 28 may form a chamber 33 there between. An airflow channel 34 may be exposed to and/or open to support portion 31 such that the airflow channel 34 may distribute airflow passing through a TED 35 to different portions of the cushion 22 and/or seatback 24. One or more configurations may be available to distribute airflow passing through the TED 35 to the different portions of the cushion 22 and/or seatback 24.

For example, FIG. 6 shows the airflow channel 34 which may have an H-shape and include an inlet port 36 exposed to the TED 35. Air passing through the inlet port 36 may then distribute throughout the airflow channel 34 and may travel through support portion holes 27 and trim holes 29 to heat/cool the occupant. Different materials, such as reticulated foam and/or a breathable spacer fabric may be used for the support portion 31. The airflow channel 34 may also receive the breathable spacer fabric such that airflow may pass through portions of the fabric along the airflow channel 34.

Positioning of the climate control system 26 may vary. Preferred positions may be within and/or adjacent to the cushion 22 and the seatback 24. Each climate control system 26 may further include a blower system 30, a tube 32 and the TED 35. The blower system 30 may include a blower and blower motor to direct airflow to the TED 35 via the tube 32. However, configurations of the climate control system 26 may vary such that the blower system 30 and TED 35 may be in fluid communication without the tube 32. For example, the blower system 30 may be mounted to the TED 35 such that the blower system 30 pushes airflow directly into the TED 35. A seal 38 may be disposed between the TED 35 and inlet port 36 to prevent, reduce, and/or minimize air leakage. Air passing through the TED 35 may be heated or cooled as directed by occupant controls 40 and/or a controller. As such, air heated or cooled by the climate control system 26 may be delivered to the occupant sitting against the trim cover 28. Similarly, the heated or cooled air may be delivered to the chamber 33 when the plenum 14 is positioned against the trim cover 28 of cushion 22 or seatback 24.

Figure 3:
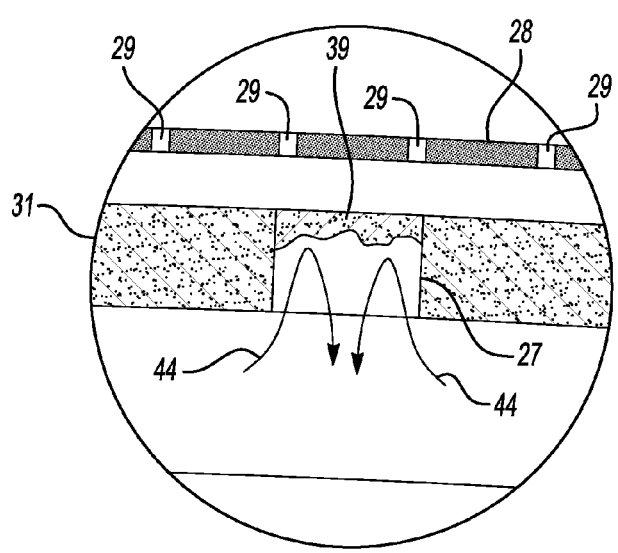
FIG. 3 is a side view, in cross-section, of an airflow fault condition in which foam flashover is obstructing an airflow hole within a climate control system of a vehicle seat.
Figure 4:
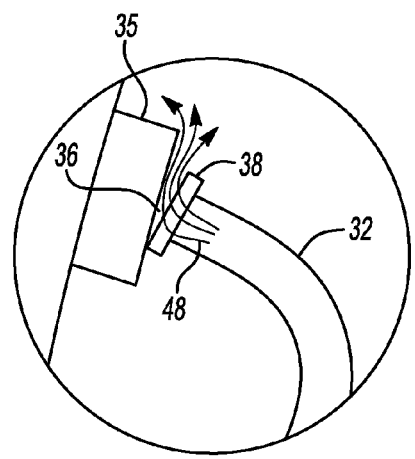
FIG. 4 is a side view, in cross-section, of an airflow fault condition in which a seal is seated improperly within a climate control system of a vehicle seat.

As mentioned above, fault conditions may occur which disrupt operation of the climate control system 26. These fault conditions may prevent, impair and/or hinder the airflow from reaching a desired temperature in a timely manner, may cause the cushion 22 and seatback 24 to heat/cool inconsistently, may prevent the cushion 22 and seatback 24 from heating/cooling at all, and/or may prevent airflow from reaching the occupant. Examples of causes for fault conditions may include (i) foam flashover, such as foam flashover in the support portion holes 27 of the support portion 31, (ii) debris obstructing airflow within the climate control system 26, and/or (iii) seal failure, such as a failure of seal 38 between the TED 35 and inlet port 36. FIG. 3 shows a scenario in which foam flashover 39 has blocked the support portion holes 27, thus preventing airflow from reaching the occupant through trim holes 29 as shown by airflow reference arrows 44. FIG. 4 shows a scenario in which a seal 38 is seated improperly and leaks air from the climate control system 26 as shown by reference arrows 48. FIG. 5 shows a scenario in which a piece of debris 46 is obstructing airflow through the tube 32 as shown by reference arrows 47.

These airflow fault conditions typically cannot be seen by an operator unless the operator tears down the seat 12 which may also require removing the seat 12 from the vehicle if already installed. Further, the operator may not know where to begin examining the seat 12 to identify the cause or causes of the airflow fault condition. However, the controller of the test apparatus 10 may be programmed to detect obstructions to or losses of airflow between the trim cover 28 and the motor of the blower system 30 by measuring and comparing a first current reading and a second current reading of the blower system 30 while applying different pressure levels to the chamber 33 and the climate control system 26.

For example, following assembly of the seat 12 at the JIT facility and prior to vehicle installation at the assembly plant, the operator may place the plenum 14 against the trim cover 28 of cushion 22 or the seatback 24. Additionally and/or optionally, the climate control systems 26 of the cushion 22 and seatback 24 may be tested together with two plenums 14. In this test scenario, each plenum 14 may be in fluid communication with the air pump arrangement 18 or separate air pump arrangements. The plenum 14 may optionally include a base 43 around a lower edge of the plenum 14 to assist in facilitating a closed and/or substantially closed pressure system of the chamber 33. Different materials may be used for the base 43 which may assist in providing a tighter fit to the trim cover 28. For example, the base 43 may be made of a material similar to a weather strip or a vinyl skirt to assist in minimizing leakage from the chamber 33. The plenum 14 may have an inlet port 49 to receive the delivery tube 16 which is in fluid communication with the air pump arrangement 18. Thus, the delivery tube 16 may facilitate a fluid communication between the air pump arrangement 18 and the chamber 33 such that the air pump arrangement 18 may also be in fluid communication with the climate control system 26.

Optionally, the plenum 14 may be configured to expand and/or contract to accommodate for various types of seats. This capability to expand and/or contract may adjust the chamber 33 and base 43 to correspond to different trim hole configurations on the various types of seats such that airflow will enter the chamber 33 from the respective climate control system.

Now referring again to FIGS. 1 and 2, the operator may connect the current meter 20 to the motor of the blower system 30 in preparation to capture the first current reading. Various connection configurations may be available to facilitate electrical communication between the motor of the blower system 30 and the current meter 20. For example, the operator may use a wire harness of the seat 12 to access a current output of the blower system 30. The operator may also connect a wire from the current meter 20 directly to the motor of the blower system 30. Once the current meter 20 is in electrical communication with the blower system 30, the operator may activate the blower system 30 and capture the first current reading. The operator may then activate the air pump arrangement 18 to lower or increase the pressure level of the chamber 33.

Once the air pump arrangement 18 is activated, the operator may capture the second current reading of the blower system 30 motor with the current meter 20. If the fluid communication between the climate control system 26 and the chamber 33 is operating properly, the second current reading of the blower system 30 may be different than the first current reading. The magnitude of this current draw difference between current readings may vary depending on the type of blower system 30 and configuration of climate control system 26. As such, an operator may establish a current draw difference range specific to the type of blower system 30 and climate control system 26 for use with testing. The range may represent a current draw spectrum associated with proper and/or improper operation and airflow of the climate control system. For example, an absolute current draw difference between the first current reading and second current reading of five percent or more may indicate little or no airflow blockage and/or leakage within the climate control system 26. Here, a lower portion of the range may be equal to 95% of the current draw of the first current reading and a higher portion of the range may be equal to 105% of the current draw of the first current reading. In this example, the controller may output a signal and/or an alert indicating that the climate control system 26 does not have an airflow fault condition. Another example of a signal and/or alert may indicate an absence of obstructions to or losses of airflow. Additionally, the operator may establish a threshold value, such as a current draw equal to 5% of the first current reading, to compare to an absolute current draw difference between the first and second current readings.

If the airflow within the climate control system 26 is operating improperly, the second current reading of the blower system 30 may be the same or substantially the same as the first current reading. Thus, the difference between the first and second readings may be approximately equal to zero when an airflow fault condition is present. Alternatively, an absolute current draw difference which is less than the established threshold value, such as a current draw equal to 5% of the first current reading, may indicate blockage and/or leakage within the climate control system 26. In this example, the controller may output a signal and/or alert indicating that the climate control system 26 has an airflow fault condition. As such, the operator may focus further evaluation and/or repair efforts on the causes for airflow fault conditions described above.

Figure 7:
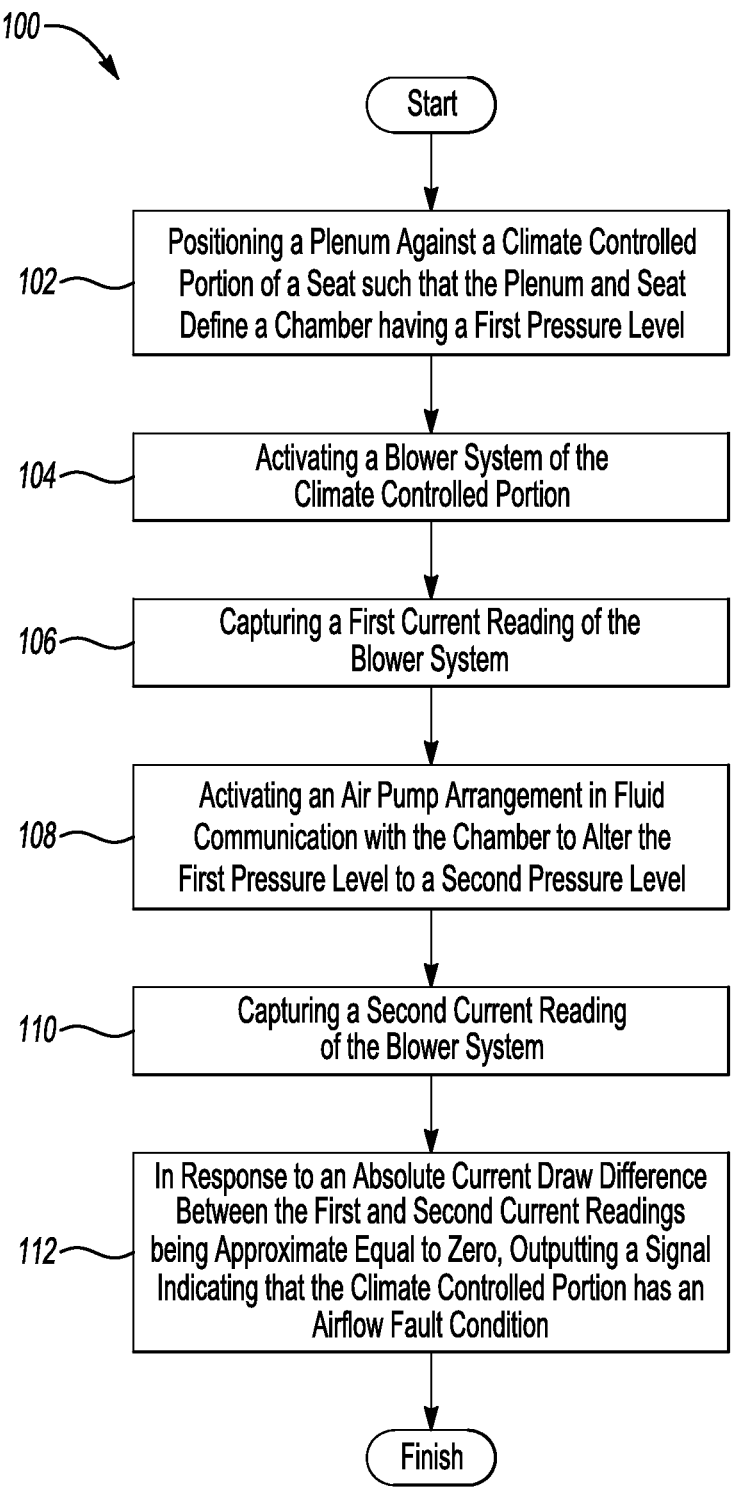
FIG. 7 is a flow chart of an algorithm for testing airflow of a climate control system of a vehicle seat.

Now referring to FIG. 7, an algorithm is generally indicated by reference numeral 100. Operation 102 may include positioning the plenum 14 against a climate controlled portion of the seat 12, for example the trim holes 29 of the cushion 22 or the seatback 24. The plenum 14 and cushion 22, or the plenum 14 and seatback 24 may define the chamber 33 having a first pressure level. The plenum 14 may be positioned such that the trim holes 29 open to the chamber 33. In operation 104, the blower system 30 may activate to direct airflow through the climate control system 26. In operation 106, the current meter 20 may capture a first current reading of the blower system 30. In operation 108, the air pump arrangement 18 may activate to reduce or increase the pressure level of the chamber 33 from the first pressure level to a second pressure level. In operation 110, the current meter 20 may capture a second current reading of the blower system 30. In response to an absolute current draw difference between the first and second current readings being approximately equal to zero, a signal may be output indicating that the climate control system 26 has an airflow fault condition in operation 112. Upon receipt of the airflow fault condition alert, operator evaluation and/or repair efforts may focus on the causes for airflow fault conditions described above.

Additional and/or optional responses may also be output during operation 112. For example, operation 112 may output a signal indicating that the climate control system 26 has an airflow fault condition in response to an absolute current draw difference between the first and second current readings being less than a threshold value. As another example, operation 112 may output a signal indicating that the climate control system 26 does not have an airflow fault condition in response to the absolute current draw difference between the first and second current readings being greater than the threshold value.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

What is claimed is:

1. A climate controlled seat test apparatus comprising:
   a plenum adapted to be placed against an A-surface trim cover of a climate controlled portion of a vehicle seat such that the plenum and A-surface trim cover define a chamber;
   an air pump arrangement configured to alter a pressure within the chamber; and
   at least one controller programmed to detect obstructions to or losses of airflow between the A-surface trim cover and a blower motor of the climate controlled portion based on a change in current consumed by the blower motor caused by a change in pressure within the chamber, wherein the plenum and air pump arrangement define a closed system with the climate controlled portion of the vehicle seat.

2. The apparatus of claim 1, wherein the at least one controller is further programmed to output an alert indicating detection of the obstructions to or losses of airflow when the change in current consumed by the blower motor is near or equal to zero.

3. The apparatus of claim 1, wherein the at least one controller is further programmed to output an alert indicating an absence of obstructions to or losses of airflow when the change in current consumed by the blower motor is five percent or more.

4. The apparatus of claim 1, wherein the air pump arrangement is further configured to increase the pressure within the chamber.

5. The apparatus of claim 1, wherein the air pump arrangement is further configured to decrease the pressure within the chamber.

6. A method for testing a climate controlled seat comprising:
   positioning a plenum against a climate controlled portion of the seat such that the plenum and seat define a chamber and a closed system;
   capturing a first current reading of a blower motor of the climate controlled portion while the blower motor is on and a pressure within the chamber is at a first pressure;
   capturing a second current reading of the blower motor while the blower motor is on and the pressure within the chamber is at a second pressure; and
   in response to an absolute current draw difference between the first and second current readings being less than a threshold value, outputting a signal indicating that the climate controlled portion has an airflow fault condition.

7. The method of claim 6 further comprising, in response to the absolute current draw difference between the first and second current readings being near or equal to zero, outputting a signal indicating that the climate controlled portion has an airflow fault condition.

8. The method of claim 6 further comprising, in response to the absolute current draw difference between the first and second current readings being greater than the threshold value, outputting a signal indicating that the climate controlled portion does not have an airflow fault condition.

9. The method of claim 6, wherein the threshold value is a current draw equal to 5% of the first current reading.

10. A vehicle seat test apparatus comprising:
    a plenum for placement against an A-surface trim cover of a climate controlled seat portion to define an external chamber;
    an external pump arrangement to alter a pressure within the chamber or a vicinity of the seat portion; and
    a controller to detect airflow obstructions or losses within the seat portion based on change in current consumed by a seat blower caused by the pump arrangement.

11. The apparatus of claim 10, wherein the controller is further programmed to output an airflow fault condition alert when the change in current consumed by the seat blower is near or equal to zero.

12. The apparatus of claim 10, wherein the at least one controller is further programmed to output a signal indicating that the seat portion does not have an airflow fault condition when the change in current consumed by the seat blower is less than or equal to 95% of a first current reading associated with the seat blower or greater than or equal to 105% of the first current reading.

* * * * *